United States Patent [19]

Ersfeld et al.

[11] Patent Number: 4,841,958
[45] Date of Patent: Jun. 27, 1989

[54] NONWOVEN ORTHOPEDIC CASTING MATERIALS WITH APERTURES

[75] Inventors: Dean A. Ersfeld, Maplewood; Paul E. Hansen, Lake Elmo, both of Minn.

[73] Assignee: Minnesota Mining and Manufacturing Company, St. Paul, Minn.

[21] Appl. No.: 47,006

[22] Filed: May 5, 1987

[51] Int. Cl.$^4$ .............................................. A61F 5/04
[52] U.S. Cl. ................................... 128/90; 128/89 R; 427/2; 428/423.1; 428/425.6; 428/913
[58] Field of Search ................. 128/90, 91 R, 89 R, 128/156, 169; 28/105; 427/2; 428/290, 423.7, 423.1, 425.6, 253, 352, 913

[56] References Cited

U.S. PATENT DOCUMENTS

| | | | |
|---|---|---|---|
| 3,332,416 | 7/1967 | Brickman et al. | 128/91 R |
| 3,485,706 | 12/1969 | Evans | 161/72 |
| 3,681,184 | 3/1970 | Kalwaites | 161/109 |
| 3,682,756 | 3/1970 | Kalwaites | 161/109 |
| 3,972,323 | 8/1976 | Boricheski | 128/91 R |
| 4,238,522 | 12/1980 | Potts | 128/90 |
| 4,272,848 | 6/1981 | Hoofnagle | 2/2 |
| 4,287,251 | 9/1981 | King et al. | 128/156 |
| 4,376,438 | 3/1983 | Straube et al. | 128/90 |
| 4,411,262 | 10/1983 | von Bonin et al. | 128/90 |
| 4,502,479 | 3/1985 | Garwood et al. | 128/90 |
| 4,570,622 | 2/1986 | von Bonin et al. | 128/90 |
| 4,609,578 | 9/1986 | Reed | 428/76 |
| 4,627,424 | 12/1986 | Baron et al. | 128/91 R |
| 4,638,795 | 1/1987 | Richter et al. | 128/90 |
| 4,667,661 | 5/1987 | Scholz et al. | 128/90 |
| 4,705,840 | 11/1987 | Buckanin | 528/53 |

FOREIGN PATENT DOCUMENTS 2092606 8/1982 United Kingdom

OTHER PUBLICATIONS

Isaacs (editor), "Textile World Manmade Fiber Chart 1986", McGraw-Hill (1986).
"Introducing the World-Class Watered Down Idea," a product brochure of Honeycomb Systems, Inc., Biddeford, Me.
"Features of Sontara," a product brochure of E. I. DuPont de Nemours and Company, Wilmington, Del.
"Creative Concepts for Tomorrow's Applications-Kendall Nonwovens,", a product brochure of the Kendall Company, Boston, Mass.

Primary Examiner—Richard J. Apley
Assistant Examiner—Paul Prebilic
Attorney, Agent, or Firm—Donald M. Sell; Walter N. Kirn; Dale E. Hulse

[57] ABSTRACT

The present invention relates to orthopedic casting materials and methods for preparing and using such orthopedic casting materials, wherein the materials comprise a nonwoven, stretchable fabric which is impregnated with a curable prepolymer resin. The nonwoven fabric comprises fiber bundles and apertures between the fiber bundles, with each of the fiber bundles comprising a plurality of fibers having interstices therebetween. The curable prepolymer resin is impregnated into the nonwoven fabric such that the interstices between the fibers receive the resin, while leaving the apertures between fiber bundles substantially unoccluded. Such orthopedic casting materials are relatively inexpensive and exhibit improved properties.

51 Claims, 4 Drawing Sheets

NONWOVEN ORTHOPEDIC CASTING MATERIALS WITH APERTURES

BACKGROUND

1. The Field of the Invention

The present invention relates to novel orthopedic casting materials, and in particular, to orthopedic casting materials and methods employing a nonwoven fabric.

2. The Prior Art

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Paris casts typically disintegrate in water, thus making it necessary to avoid bathing, showering, or other activities involving contact with water. In addition, plaster of Paris casts are not air permeable, and thus do not allow for the circulation of air beneath the cast which greatly facilitates the evaporation and removal of moisture trapped between the cast and the skin. This often leads to skin maceration, irritation, or infection. Such disadvantages, as well as others, stimulated research in the orthopedic casting art for casting materials having improved properties over plaster of Paris.

A significant advancement in the art was achieved when polyisocyanate prepolymers were found to be useful in formulating a resin for orthopedic casting materials, as disclosed, for example, in U.S. Pat. No. 4,502,479 (Garwood et al.). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. No. 4,502,479 provide significant advancements over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit materials are not as compressible as plaster, and tend to mask the fine structure of the bone as the cast is applied. Moreover, orthopedic casting materials involving knit fabrics such as fiberglass are somewhat expensive, and may be cost prohibitive for some users.

An example of an orthopedic bandage using a polyester fabric which is not a knitted fabric is disclosed in U.S. Pat. No. 3,972,323 (Boricheski). However, the orthopedic bandage disclosed in U.S. Pat. No. 3,972,323 involves the use of plaster of Paris, and thus is subject to the disadvantages outlined hereinabove for plaster of Paris orthopedic casts, including an inferior strength-to-weight ratio and poor air permeability.

From the foregoing, it will be appreciated that what is needed in the art is an orthopedic casting material which has both the advantages of plaster of Paris, e.g., good moldability and palpability of the fine bone structure, and the advantages of non-plaster of Paris materials, e.g., good strength-to-weight ratio and good air permeability. In this regard, it would be a significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the non-plaster of Paris orthopedic casting materials of the prior art, and which can be made to be significantly less expensive, and therefore less cost prohibitive, than prior art orthopedic casting materials employing knitted fabrics. Such orthopedic casting materials and methods for preparing the same are disclosed and claimed herein.

BRIEF SUMMARY AND OBJECTS OF THE INVENTION

The present invention relates to orthopedic support materials or casting materials utilizing a nonwoven, stretchable fabric which, when loaded with resin, is easily moldable and permits good palpation of bone structure during application. The nonwoven fabric is preferably made of a relatively inexpensive material, such as a presently preferred nonwoven polyester material. The nonwoven fabric comprises fiber bundles and apertures between the fiber bundles, with each of the fiber bundles comprising a plurality of fibers having interstices therebetween. A curable prepolymer resin such as an isocyanate functional, polyurethane prepolymer resin is impregnated into the interstices between the fibers of each fiber bundle so as to impart sufficient strength to the material upon curing to be used as an orthopedic casting material, while leaving the apertures between fiber bundles substantially unoccluded so as to produce a porous finished cast which permits sufficient water vapor permeability therethrough to substantially avoid skin maceration.

Such orthopedic casting materials not only exhibit better moldability and palpability than prior art non-plaster of Paris casting materials, but may also be made to be significantly less expensive than prior art non-plaster of Paris casting materials. The orthopedic casting materials of the present invention preserve the advantages characteristic of non-plaster of Paris materials, and in some instances provide additional advantages. In this regard, the orthopedic casting materials of the present invention have been found to exhibit improved resin holding capacity and other improved properties over prior art non-plaster of Paris orthopedic casting materials.

It is, therefore, an object of the present invention to provide orthopedic casting materials which avoid the use of plaster of Paris, which exhibit good conformability and moldability, and which allow for good tactile manipulation and good palpation of the bone structure through the casting materials.

Another object of the present invention is to provide orthopedic casting materials which have improved resin holding capacity while maintaining good water vapor permeability.

A further object of the present invention is to provide orthopedic casting materials which are significantly less expensive than other non-plaster of Paris prior art casting materials.

These and other objects and features of the present invention will become more fully apparent from the following description and appended claims, taken in conjunction wit the accompanying drawings.

DETAILED DESCRIPTION OF THE PREFERRED EMBODIMENTS

Figure 1A:
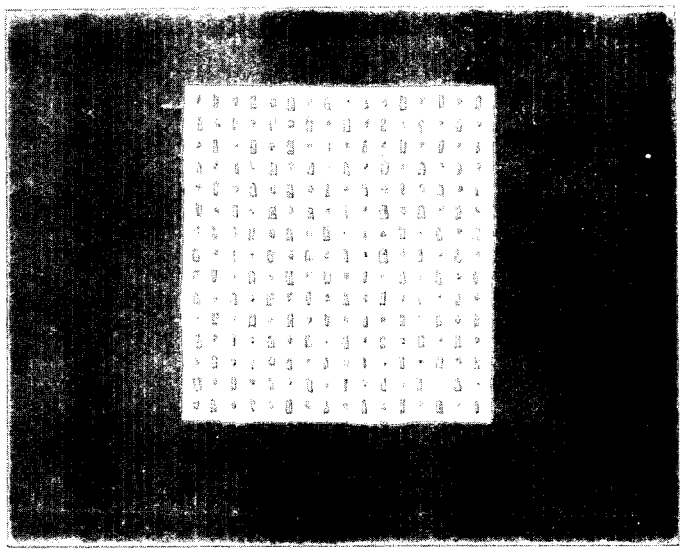
FIG. 1A is a photograph (taken to scale) of one presently preferred nonwoven fabric which can be used in accordance with the present invention, and which fabric is available from E. I. duPont de Nemours and Company, Textile Fibers Dept., Centre Road Bldg., Wilmington, Del., as Sontara ® polyester fabric, style 8043. In this and all other figures herein, the longitudinal or elongated direction of the nonwoven fabric is from top to bottom.
Figure 1B:
FIG. 1B is a photograph of a portion of the nonwoven fabric of FIG. IA shown at a magnification of five times (5×) that of FIG. 1A.
Figure 1C:
FIG. 1C is a photograph of a portion of the nonwoven fabric of FIG. 1A shown at a magnification of ten times (10×) that of FIG. 1A.
Figure 2A:
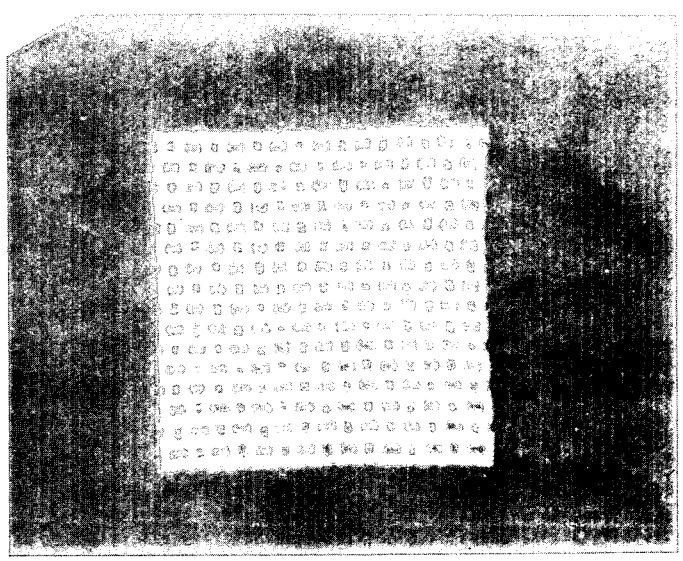
FIG. 2A is a photograph (taken to scale) of another presently preferred nonwoven fabric which can be used in accordance with the present invention, and which fabric is available from E. I. duPont de Nemours and Company as Sontara ® polyester fabric, conformable style 8043, set 2, 8 mesh, condition A.
Figure 2B:
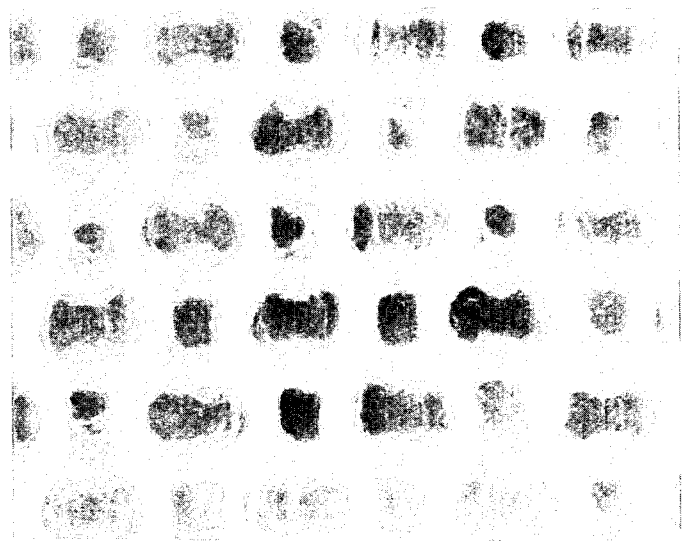
FIG. 2B is a photograph of a portion of the nonwoven fabric of FIG. 2A shown at a magnification of five times (5×) that of FIG. 2A.
Figure 2C:
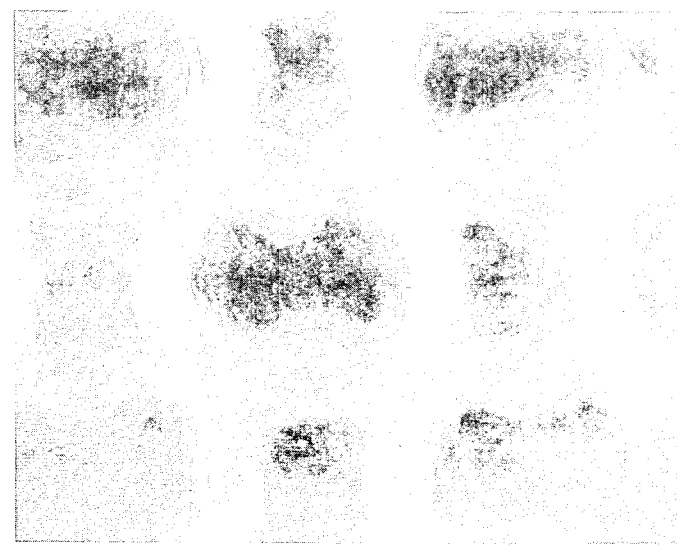
FIG. 2C is a photograph of a portion of the nonwoven fabric of FIG. 2A shown at a magnification of ten times (10×) that of FIG. 2A.

The present invention relates to orthopedic casting materials and methods for preparing and using such orthopedic casting materials, wherein the materials comprise a nonwoven, stretchable fabric which is impregnated with a curable prepolymer resin. In particular, the nonwoven fabrics employed in the present invention have important surface characteristics and physical properties which allow the nonwoven fabrics to be resin loaded to the extent needed to provide proper strength as an orthopedic casting material, while providing necessary porosity as well as improved tactile manipulability, moldability, and palpability. At the same time, the orthopedic casting materials of the present invention are relatively inexpensive, thus providing a more economical alternative to the non-plaster of Paris orthopedic casting materials presently known in the art which employ knitted fabrics.

In this regard, those skilled in the art have generally considered nonwoven fabrics undesirable as a support material or scrim in an orthopedic casting material which employs a curable resin, and have generally sought to use knitted materials for this purpose. However, applicants have discovered certain surface properties and other fabric characteristics which, when incorporated into a nonwoven fabric as disclosed herein, provide a fabric which can be resin loaded to the extent necessary to provide an orthopedic casting material having sufficient strength to be used efficaciously in forming an orthopedic cast or splint, while at the same time exhibiting the conformability and moisture vapor transmission necessary in orthopedic applications.

The stretchable, nonwoven fabric comprises fiber bundles and apertures between the fiber bundles, with each of the fiber bundles comprising a plurality of fibers having interstices therebetween. (Thus, the nonwoven fabrics of the present invention are sometimes referred to as "apertured," "ordered," or "patterned" nonwoven fabrics.) The fibers in each fiber bundle of the nonwoven fabric are preferably oriented so as to be generally parallel to one another. The interstices between the fibers of each fiber bundle receive the curable resin so as to impart strength to each fiber bundle upon curing. The generally parallel orientation of the fibers in each fiber bundle provides significantly greater resin holding capacity (and thus greater strength upon curing) than would be achieved if the fibers were randomly oriented. However, the apertures between fiber bundles, are substantially free of fibers such that, upon resin impregnation of the fiber bundles, the apertures remain substantially unoccluded so that sufficient water vapor permeability in the finished cast is preserved, and disadvantages such as potential skin maceration are substantially avoided.

The interstices between individual fibers and the apertures between fiber bundles for two presently preferred nonwoven fabric materials are seen in FIGS. 1A-1C and 2A-2C. As seen in FIGS. 1A-1C and 2A-2C, the multiple fiber bundles of the nonwoven fabrics of the present invention form a matrix. Further, the characteristics of these fabrics after resin impregnation and lamination can be viewed in FIGS. 3A-3C and 4A-4C. The foregoing structural characteristics of the nonwoven fabrics of the present invention, in conjunction with the other characteristics and parameters disclosed herein, provide fabrics which can be resin loaded to the extent necessary to impart sufficient strength, while preserving air permeability through the material.

In conjunction with the structural configuration discussed above, the most important criteria for choosing a nonwoven fabric which will provide the characteristics necessary for purposes of the present invention include: (1) conformability, and the related characteristics of moldability, tactility, and palpability once the fabric has been resin impregnated; (2) resin loading capacity; and (3) porosity. It is important that each of these parameters be carefully controlled in providing nonwoven fabrics which will successfully form orthopedic casting materials within the scope of the present invention.

Conformability is important from the standpoint that the nonwoven fabric must be extensible enough along its length, i.e., in the elongated direction, so that the resultant orthopedic casting material can be made to substantially conform to the body part to which it is applied. Materials which are not sufficiently extensible in the elongated direction do not conform well to the body part when wrapped therearound, often resulting in undesirable wrinkles or folds in the material. On the other hand, the extensibility of the nonwoven fabric in the elongated direction should not be so high that the material is too stretchy, resulting in a material structure which may be deformed to the extent that resin holding capacity and porosity are substantially reduced.

With these criteria in mind, for purposes of the present invention, the nonwoven fabric should have from about 10% to about 45% extensibility in the elongated direction when a 2 pound (908 gram) load or force is applied across a 1.5 inch (3.8 cm) section of the nonwoven fabric, and preferably from about 15% to about 30% extensibility in the elongated direction when a 2 pound (908 gram) load or force is applied across a 1.5 inch (3.8 cm) section of the nonwoven fabric.

Although not nearly as critical, it is also desirable that the nonwoven fabric employed have some extensibility along its width, i.e., in the direction transverse to the elongated direction. Thus, although the nonwoven fabric may have from 0% to 100% extensibility in the transverse direction, it is presently preferable to use a nonwoven fabric having from about 1% to about 30% extensibility in the transverse direction when a 2 pound (908 gram) load or force is applied across a 1.5 inch (3.8 cm) section of the nonwoven fabric.

The nonwoven fabrics of the present invention, although stretchable, are preferably not elastic or resilient. Thus, once the resin impregnated fabric has been stretched and applied around a body part, the stretched material maintains its shape and does not resort back to its unstretched position.

The resin loading capacity or ability of the nonwoven fabric to hold resin is important from the standpoint of providing an orthopedic casting material which has sufficient strength to efficaciously immobilize a body part. The surface structure of the nonwoven fabric, including the fibers and fiber bundles, interstices, and apertures discussed herein, is very important in providing proper resin loading for purposes of the present invention. In this regard, the interstices between the fibers of each fiber bundle must provide sufficient volume or space to hold an adequate amount of resin within the fiber bundle to provide the strength necessary; while at the same time, the apertures between fiber bundles must remain sufficiently unoccluded such that adequate porosity is preserved once the resin is applied. (Generally parallel orientation of the fibers in the fiber bundles provides interstices which optimize resin holding capacity and resultant strength of the material upon curing.) Thus, the interstices between fibers are important in providing the necessary resin loading capacity, while the apertures are important in providing the necessary porosity for the finished cast. However, a balancing of various parameters is needed to achieve both proper resin loading and porosity.

For purposes of the present invention, it has been found that he nonwoven fabric should be structured such that it can be resin loaded to the point where the resin from about 65% to about 90% by weight of the total weigh of the orthopedic casting material, and preferably from about 80% to about 87% by weight of the orthopedic material. Further in this regard, it has been found that in order to provide proper resin loading within scope of the present invention, from about 0.1 to 0.3 grams of resin should be applied to each square inch of the nonwoven fabric, with the preferred range of resin being from about 0.16 to about 0.24 grams of resin per square inch of nonwoven fabric. If resin loading significantly less than that disclosed herein is employed, the lamination strength of the orthopedic casting material will be compromised. On the other hand, if resin loading significantly higher than that disclosed herein is employed, porosity may be sacrificed by the undesirable occlusion of the apertures of the nonwoven fabric.

Other factors which are helpful in providing for proper resin loading of the nonwoven fabric of the present invention include the average cross-sectional area covered by each fiber bundle, the average number and size of fibers in each fiber bundle, the average volume or space between fibers in each fiber bundle, and the basis weight of the nonwoven fabric employed. In this regard, it has been found desirable to select a nonwoven fabric wherein the transverse cross-section of each fiber bundle of the nonwoven fabric covers an average area of from about 0.2 mm$^2$ to about 1.2 mm$^2$, and preferably from about 0.4 mm$^2$ to about 1 mm$^2$. Further, it is desirable that each fiber bundle contain an average of at least about 100 fibers along a given cross-section, and preferably at least about 200 fibers. The average diameter of the individual fibers in each fiber bundle is preferably from about 1 micron to about 30 microns, and most preferably from about 5 microns to about 20 microns. Additionally, of the total volume, occupied by a given fiber bundle (including both fibers and interstices), it is desirable that the average volume defined by the interstices alone (also known as the void volume) represent from about 20% to about 98% of such total volume, and preferably from about 70% to about 96% of the total volume. Moreover, it is desirable to use a nonwoven fabric having a basis weight of from about 1 ounce per square yard (34.0 g/m$^2$) to about 2.5 ounces per square yard (84.9 g/m$^2$), and preferably from about 1.2 ounces per square yard (40.8 g/m$^2$) to about 2.1 ounces per square yard (71.3 g/m$^2$).

The range of values given above for the average volume defined by the interstices (or average void volume) for the various nonwoven fabrics within the scope of the present invention was determined using the following procedure. First, a representative fiber bundle was taken from each nonwoven fabric and mounted in epoxy. Next, thin cross-sections of each fiber bundle were microtomed from this. The number of fibers per bundle was estimated under magnification (53×) with cross polarized light. The cross-sectional area of the fiber bundle was estimated from a photomicrograph (taken at 53× magnification). The average fiber diameter was estimated by examining the individual fibers at 400× magnification. The total estimated volume occupied by the fiber bundle and the estimated volume occupied only by the fibers in the bundle were then calculated. The estimated volume occupied by the fibers was then subtracted from the total estimated volume of the fiber bundle, and this difference was divided by the total estimated volume of the fiber bundle and multiplied by 100 to give the estimated percent void volume.

As mentioned, porosity is also an important characteristic for the nonwoven fabrics of the present invention. If the orthopedic casting material is not sufficiently porous after curing, skin maceration and other undesirable problems may occur. As will be appreciated from the discussion herein relating to resin loading of the nonwoven fabric, porosity and resin loading are often influenced by similar factors, and thus a balance must be achieved. (For example, where a nonwoven fabric is employed having a basis weight towards the lower end of the ranges set forth herein, resin loadings at the lower end of the ranges set forth herein may be most suitably employed. Conversely, when higher basis weights are employed, higher resin loadings are generally more suitable.)

Of key importance in providing adequate porosity is the number of apertures per unit area and the size of the apertures between the fiber bundles. In this regard, it has been found desirable to use a nonwoven fabric having from about 15 to about 400 apertures per square inch of nonwoven fabric, and preferably, from about 35 to about 170 apertures per square inch of nonwoven fabric. Additionally, it is desirable to use a nonwoven fabric having an average aperture size of from about 0.3 square millimeters (0.3 mm$^2$) to about 16 mm$^2$, and preferably having an average aperture size of from about 1.2 mm$^2$ to about 9 mm$^2$. Aperture sizes significantly lower than those disclosed herein typically do not allow sufficient air permeability to provide the porosity needed for a suitable orthopedic casting material. Aperture sizes much greater than those disclosed herein result in an aesthetically undesirable increase in surface roughness, and may not provide enough fiber bundles per unit area such that resin loading of the fiber bundles can result in a material having sufficient strength in relatively few layers.

The aperture sizes disclosed herein are large enough that the resin will migrate to and associate with the fiber bundles so as to leave the apertures substantially unoccluded. In this regard, it is desirable that an average aperture size be selected such that, when resin loading within the ranges disclosed herein is employed, from about 60% to about 100% of the total area of the apertures remains unoccluded after impregnation of the nonwoven fabric with the curable resin, and preferably such that from about 75% to about 100% of the total area of the apertures remains unoccluded after resin impregnation. By so doing, sufficient air permeability can be achieved so that adequate water vapor transmission in the finished cast is provided.

For purposes of the present invention, the total area of the apertures remaining unoccluded after resin impregnation of each nonwoven fabric was determined as follows. First, a 3 inch (7.6 cm) by 8 inch (20.3 cm) piece of each fabric was cut out, and two areas about 1.5 cm by 1.5 cm were selected and marked. A photograph of each marked area was then taken at 5× magnification. The piece of fabric was then impregnated with the desired amount of curable resin, and photographs of the two marked areas were again taken at 5× magnification. In each photograph of uncoated fabric, twenty apertures were selected and measured, and the same apertures were located and measured in the photographs taken after resin impregnation. The selected apertures were measured in each photograph by estimating the length and width in millimeters at approximately the middle of each aperture. The mean area of the apertures in each marked area of the fabric before and after resin impregnation was then estimated by first dividing the length and width measured in the photographs by 5 (to compensate for the magnification factor), and then multiplying the resultant two figures together. By subtracting the mean aperture area of the resin impregnated fabric from that of the uncoated fabric, and dividing the result by the mean aperture area of the uncoated fabric, the fraction of aperture area occluded by resin was calculated. The percentage of the total aperture area remaining unoccluded by resin was then determined by subtracting the above number from 1 and then multiplying by 100.

By employing nonwoven fabrics having the characteristics discussed herein, orthopedic casting materials are provided which have good water vapor permeability for orthopedic applications. Upon curing a 6 layer ring laminate of the orthopedic casting material, the, laminate has a passive water vapor permeability of at least about 2000 milligrams of water vapor per square meter of material per hour (2000 mg H$_2$O vapor/m$^2$-hr) when measured under an atmosphere of about 45% relative humidity and at a temperature of about 72° F. (22° C.), and in the most preferable embodiments of the present invention at least about 2200 mg H$_2$O vapor/m$^2$-hr when measured under the same conditions.

The passive water vapor permeability of orthopedic casting materials made in accordance with the present invention has been measured using the following procedure. Test rings having an inside diameter of 2 inches (5.1 cm) and a length of 3 inches (7.6 cm) were first prepared from the orthopedic casting materials by dipping the materials in water for about 30 seconds at room temperature and wrapping 6 layers of each material around a polyester stockinet covered aluminum mandrel having a 2 inch (5.1 cm) diameter. The layers were smoothed down with light hand pressure, and after becoming rigid, each ring was removed from the mandrel (with the stockinet adhering to the inside of the ring) and allowed to dry and cure at room temperature for at least 24 hours. After such time, one end of each ring was sealed with a plastic petri dish using a silicone based sealant, namely RTV 732 Silastic TM, available from Dow Corning, Midland, Mich. A small beaker containing about 30 grams of water was placed inside each ring, and the other end of each ring was then also sealed with a plastic petri dish using RTV 732 Silastic TM, Each sample so prepared was initially weighed, and then weighed at periodic intervals until over 300 hours had elapsed. The amount of water vapor having passed through each ring was then determined by calculating the difference in weight from start to finish.

When an air pressure differential of about 6.4 psi (absolute) or 449 g/cm$^2$ is imposed between two sides of a 6 layed laminate (with each layer having an area of about 4 in$^2$) of the cured orthopedic materials of the present invention, an air permeability of from about 30 cm$^3$ air/second to about 370 cm$^3$ air/second is achieved, with an air permeability of from about 90 cm$^3$ air/second to about 370 cm$^3$ air/second being observed in the most presently preferred embodiments of the present invention. (Although the relative humidity and temperature are not as critical here as for the passive water vapor permeability tests, it should be noted that these forced air permeability values were determined under an atmosphere of about 45% relative humidity and at a temperature of about 22° C., in accordance with the procedure outlined below). Thus, it is evident that the present invention provides the air permeability necessary and important to orthopedic applications.

For purposes of the present invention, the air permeability of each cured material was determined as follows.

First, 2 inch (5.1 cm) by 48 inch (121.9 cm) strips of each fabric were cut out, impregnated with the desired amount of curable resin, fan folded, and sealed in an air-tight pouch. Later, each pouch was opened, the folded strip of fabric was dipped in room temperature tap water for about 30 seconds, and then a six layer laminate (each layer being about 2 inches (5.1 cm) by 2 inches (5.1 cm)) was made by quickly unfolding the wet strip and fan folding it onto a polyester stockinet lying on a flat surface until six layers were formed; the strip was cut and the procedure repeated four times to form four different laminates. The six layers in each laminate were secured together by firmly rubbing an extended finger across each laminate and then continuing to smooth each laminate with light finger pressure until set. After setting, each laminate was separated from its respective stockinet. Twelve hours later, a ½ inch (1.3 cm) diameter disk of 3M brand Microfoam ® tape was placed on each side of each laminate in approximately the center so that the disks were lined up, one directly above the other. Each laminate was then coated over both surfaces with RTV 732 sealant (Dow Corning, Midland, Michigan) to occlude the unmasked areas and provide a gasket for the air permeability measuring device. The sealant was cured by placing each coated laminate in an oven at 120° F. (49° C.) for at least 2 hours. Each coated laminate was then in turn placed between the upper and lower clamping plates of a Gurley Densometer No. 4110, and the lower plate was raised to seal the laminate between the plates with the masked area approximately centered. The inner cylinder was freed to sink. If the cylinder stopped sinking or sank only very slowly, the seal was considered adequate. (Otherwise, another layer of RTV sealant was applied to both sides and cured.) The laminate was then removed from the Densometer, and the Microfoam tape was removed exposing a ½ inch (1.3 cm) diameter circular area of substrate on both sides of the laminate. The laminate was then again clamped between the plates and the time measured for the inner cylinder (weighing 20 oz.) to drop a distance corresponding to the passage of 300 cm$^3$ of air under a pressure differential of 6.4 psi (absolute) or 449 g/cm$^2$. This was repeated three more times, and the longest time noted for each laminate was taken as a measure of its air permeability. The volume of air passed per second was calculated by dividing 300 cm$^3$ by the mean time determined on 4 samples for passage of this volume of air.

Although apertured and stretchable nonwoven fabrics meeting the criteria set forth herein may be prepared by various methods, the presently most preferred nonwoven fabrics are prepared by well-known techniques which yield what are known as "spunlaced" and "hydroentangled" nonwoven fabrics. The term "spunlaced fabric" generally refers to a nonwoven fabric formed of fibers entangled in a predetermined and repetitive pattern to form a strong structure free of binder material. Typically, in producing a spunlaced fabric, a fibrous support web is subjected to high velocity water jets that entangle the fibers and thereby achieve mechanical bonding of the fibers. This process is the reason that such nonwoven fabrics are typically referred to as "hydroentangled fabrics," the fabrics being formed through entanglement achieved by water jets. In this regard, the high pressure water jets typically entangle the fibers at velocities of up to 100 meters/second. The fibrous support web is patterned in accordance with the desired pattern of the nonwoven fabric to be formed.

Thus, when the jets of water are applied both above and beneath the fibrous support web, the fibers are oriented into a pattern of fiber bundles and apertures according to the pattern on the fibrous support web.

Processes such as that disclosed herein for forming spunlaced and hydroentangled nonwoven fabrics are well known to those skilled in the art. One such process is detailed, for example, in *Guide to Nonwoven Fabrics*, (1978), published by the INDA Association of the Nonwoven Fabrics Industry, 1700 Broadway (25th Floor), New York, N.Y. 10019, which publication is incorporated herein by reference. Additionally, spunlaced and hydroentangled nonwoven fabrics and processes for preparing the same are disclosed in U.S. Pat. No. 3,485,706, which is also incorporated herein by reference.

The selection of an appropriate material for the nonwoven fabrics of the present invention is necessarily influenced by the fact that the resultant nonwoven fabric must have the properties outlined herein. Preferably, for purposes of the present invention, the material is also relatively inexpensive. Relatively inexpensive materials which have been found suitable for the nonwoven fabrics of the present invention include polyester materials which may be easily processed at relatively low cost or which may be readily obtained. Such polyester nonwoven fabrics are presently preferred.

The presently most preferred nonwoven fabric materials are the Sontara ® polyester fabrics, which are spunlaced and hydroentangled fabrics manufactured by E. I. duPont de Nemours and Company, Textile Fibers Dept., Centre Road Bldg., Wilmington, Del. More particularly, the nonwoven polyester fabrics known as Sontara ® polyester fabric, style 8043 and Sontata ® polyester fabric, conformable style 8043, set 2, 8 mesh, condition A are materials which have been found to work extremely well for purposes of the present invention. These two polyester fabrics are the subject of FIGS. 1A-1C and 2A-2C, respectively.

The nonwoven polyester fabric materials such as the Sontara ® polyester materials referenced herein exhibit all of the desirable and necessary properties outlined herein for successfully practicing the present invention. Further, these nonwoven polyester fabric materials have been found to have high bulk at low weight, good conformability, good wet and dry strength per unit of weight, good cover and uniformity, do not unravel or delaminate, and are inherently low linting.

Other materials which may be used to form the nonwoven fabrics of the present invention include cotton, nylon, acrylic, polypropylene, fiberglass, polyarylamide, and carbon (graphite). These materials, however, are not presently preferred over the above-mentioned polyester materials, primarily because of their increased cost. In this regard, cotton, nylon, acrylic, polypropylene, and fiberglass are somewhat more expensive than the preferred polyester materials, while polyarylamide and carbon are quite significantly more expensive.

Moreover, those skilled in the art will recognize that fiberglass nonwoven materials have a significantly higher density than the other materials disclosed herein. Thus, when fiberglass nonwoven materials are employed, the basis weight of the material and weight percent of resin employed will vary from the values set forth herein. In this regard, when fiberglass is used, the nonwoven fabric should have a basis weight of from about 1.8 ounces per square yard (61.1 g/m$^2$) to about 4.6 ounces per square yard (156.3 g/m$^2$), preferably from about 2.2 ounces per square yard (74.7 g/m$^2$) to about 3.6 ounces per square yard (122.3 g/m$^2$), and the fiberglass nonwoven fabric should be resin loaded such that the resin represents from about 35% to about 90% by weight of the total weight of the orthopedic casting material, preferably from about 50% to about 87% by weight.

The importance of selecting a nonwoven fabric in accordance with the criteria set forth herein is further seen in view of the number of nonwoven fabrics which are not suitable for purposes of the present invention, including for example, bonded air-laid or carded web materials, wet formed random bonded web materials, Thinsulate ® brand blown microfiber web materials, and thin foam materials.

In this regard, although bonded air-laid or carded web materials coated with resin have fair porosity and good strength upon curing, the resin holding capacity of such materials is not sufficient nor is the degree of extensibility needed for proper conformability sufficient for purposes of the present invention. Similarly, wet formed random bonded web materials suffer from poor resin holding capacity and poor conformability, and when coated with a resin, such materials also exhibit poor porosity. Further, although the Thinsulate ® brand blown microfiber web materials exhibit relatively good resin holding capacity, the cohesion of the scrim structure and porosity of the cured products formed from these materials are inadequate for purposes of the present invention. Additionally, although thin foam materials (having a thickness of 1/16 of an inch or less) have good conformability, these materials also exhibit inadequate resin holding capacity to be used with the present invention. The failure of these and other nonwoven fabrics or materials demonstrates the need to balance resin holding with porosity, conformability with tensile strength (cohesion), and ultimate structural strength with material tactility (the ability to feel through the fabric). Hence, the selection of an appropriate nonwoven fabric in accordance with the criteria set forth herein is very important to the successful practice of the present invention.

The curable resins impregnated into the nonwoven fabrics of the present invention are generally flowable at room temperature. Although such flowablity could well result in the escape or loss of significant amounts of resin from other more conventional nonwoven materials, the exceptional resin holding capacity of the nonwoven fabrics of the present invention substantially prevents such escape or loss.

The curable resins which may be used to impregnate the nonwoven fabrics of the present invention include any resins which will provide the resin loading and porosity characteristics outlined herein. Preferred resins include isocyanate functional, polyurethane prepolymer resins. When using such resins, orthopedic casting materials can be prepared which, upon reaching full cure, exhibit a ring strength of at least about 10 pounds/inch (pounds per inch of cylinder length when using a cylinder 3 inches (7.6 cm) long and 2 inches (5.1 cm) in diameter which is prepared in accordance with the procedure set forth herein for preparing 6 layer test rings useful in the determination of passive water vapor permeability) or 1.79 kg/cm, with ring strengths of at least about 20 pounds/inch or 3.57 kg/cm being characteristic of the most presently preferred embodiments of the present invention. That such strength can be achieved by resin loading a nonwoven fabric in accordance with the present invention is one of the surprising benefits which has been discovered. Other surprising benefits include the relative smoothness of the resultant orthopedic casting material and the ability of the material to resist fraying.

The curable resins used in the present invention are crosslinkable to a thermoset state. Preferably, the curable resins have viscosities within the range of from about 5000 centipoise to about 500,000 centipoise, and most preferably within the range of from about 10,000 centipoise to about 100,000 centipoise. The resin should be nontoxic in the sense that it does not give off significant amounts of toxic vapors during curing which may be harmful to either the patient or the person applying the orthopedic casting material, and also in the sense that it does not cause skin irritation either by chemical irritation or by the generation of excessive heat during cure. Furthermore, the resin must be sufficiently reactive with the curing agent, (e.g., water, where water curable resins are concerned) to ensure rapid hardening of the orthopedic casting material once it has been applied, but not so reactive that it does not allow for sufficient working time to apply and shape the orthopedic cast or splint. Initially, the orthopedic casting material must be pliable short time following the completion of application, it should become rigid, or at least semirigid, and strong enough to support the loads and stresses to which the cast or splint is subjected by the activities of the wearer. Thus, the orthopedic casting material must undergo a change of state from a flexible condition to a relatively rigid condition in a matter of minutes.

The presently preferred resins are those which are cured with water. A number of classes of water curable resins are known in the art and are suitable for purposes of the present invention, including polyurethanes, cyanoacrylate esters (preferably used in conjunction with a suitable filler material such as polycyanoacrylate), and, when combined with moisture sensitive catalysts, epoxy resins and prepolymers terminated at their ends with trialkoxy-silane or trihalo-silane groups. With regard to the epoxy resins, it is noted that U.S. Pat. No. 3,932,526 discloses 1,1-bis(perfluoromethylsulfonyl)-2-aryl ethylenes which cause epoxy resins containing traces of moisture to become polymerized.

Resin systems other than those which are water curable may be used, although the use of water to activate the hardening of the orthopedic casting materials is presently the most convenient, safe, and familiar to orthopedic surgeons and medical casting personnel. For example, resin systems employing difunctional acrylates or methacrylates, such as the bis-methacrylate ester disclosed in U.S. Pat. No. 3,908,644, which ester is derived from the condensation of glycidyl methacrylate and bisphenol A (4,4'-isopropylidenediphenol), may be used. Such a resin system is hardened upon wetting with solutions of a tertiary amine and an organic peroxide. Further, U.S. Pat. No. 3,630,194 discloses an orthopedic tape impregnated with acrylamide monomers whose polymerization is initiated by dipping the orthopedic tape in an aqueous solution of oxidizing and reducing agents (known in the art as a redox initiator system).

The presently preferred resins used in conjunction with the present invention cure to form a relatively rigid structure or cast. However, in some instances such as sports medicine applications, a somewhat flexible resin may be desired to form a semi-rigid and resilient support upon curing. Examples of suitable flexible resins which may be used for this purpose are disclosed in commonly assigned copending patent application Ser. No. 903,281, filed Sept. 3, 1986, which is incorporated herein by reference.

As mentioned, the presently most preferable resins used in the present invention are water curable, isocyanate functional, polyurethane prepolymer resins. These resins are prepared by reacting a polyisocyanate with a polyol, as disclosed, for example, in U.S. Pat. Nos. 4,411,262 and 4,502,479. However, other urethane resins formed by the reaction of a polyisocyanate and a polyol, such as disclosed in U.S. Pat. No. 4,131,114, may also be used.

Thus, as used herein, a "water curable, isocyanate functional, polyurethane prepolymer" means a prepolymer derived from a polyisocyanate, preferably aromatic, and a polyol (or reactive hydrogen compound or oligomer). The polyurethane prepolymer has sufficient isocyanate functionality to cure upon exposure to water, either in the form of moisture vapor, or more preferably, in the form of liquid water.

In forming the preferred water curable, isocyanate functional, polyurethane prepolymers of the present invention, it is preferred to use an isocyanate which has a relatively low volatility, such as diphenylmethane diisocyanate (MDI), rather than a more volatile material such as toluene diisocyanate (TDI). Presently preferred isocyanates include 4,4'-diphenylmethane diisocyanate, 2,4,-diphenylmethane diisocyanate, and mixtures of these isomers together with possible small quantities of 2,2'-diphenylmethane diisocyanate (typical of commercially available diphenylmethane diisocyanate). However, isocyanates such as aromatic polyisocyanates and their mixtures which are derived from phosgenation of the condensation product of aniline and formaldehyde may also be used.

Polyols which may be used to form the polyurethane prepolymers of the present invention include polypropylene ether glycols (available from Union Carbide, Danbury, Conn. as Niax TM PPG and from BASF Wyandotte Corp., Parsippany, N.J. as Pluracol TM P), polytetramethylene ether glycols (available from the Quaker Chemical Company, Conshohocken, Pa. as Polymeg TM), polycaprolactone diols (available from Union Carbide as the Niax TM PCP series of polyols), and polyester polyols (hydroxyl terminated polyesters obtained from the esterification of dicarboxylic acids and diols such as the Lexorez TM polyols available from Inolex Corp., Chemical Division, Philadephia, Pa.). As will be appreciated by those skilled in the art, the rigidity of the cured resin can be reduced by increasing the molecular weight of the polyols, or conversely, the rigidity can be increased by using lower molecular weight polyols.

It will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121-122 (1957). Thus, for example, thiols and polyamines could also be used as "polyols" in the present invention, and the term "polyols" will be considered to include such other active hydrogen compounds.

One example of a presently preferred resin which may be used in the present invention involves the reaction of an isocyanate known as Isonate TM 143L (a mixture containing about 73% MDI) which is available from the Upjohn Company, LaPorte, Tex. with a polypropylene oxide polyol which is available from Union Carbide and is known as Niax TM PPG 725. To prolong the shelf life of the resin material, it is also preferable to include from about 0.01% to about 1% by weight of benzoyl chloride or other suitable stabilizer.

The reactivity of the curable resin, once it is exposed to the water or other curing agent, can be controlled by the use of a proper catalyst. The reactivity must not be so great that: (1) a hard film quickly forms on the resin surface preventing further penetration of the water into the bulk of the resin, or (2) the cast or splint becomes rigid before the application and shaping thereof has been completed. To produce suitable orthopedic casts and splints in accordance with the present invention, a set time of from about 2 to about 18 minutes following activation of the curable resin is preferred, with the most preferable set time being from about 3 to about 10 minutes. Thus, the curable resins of the present invention also preferably contain a catalyst to control the set time and cure time of the resin.

Suitable catalysts for moisture curing polyurethane prepolymer resin systems are well known. For example, tertiary amine catalysts such as 2,2'-dimorpholinodiethylether (DMDEE) described in U.S. Pat. No. 4,433,580, bis(2,6-dimethylmorpholino)diethylether described in U.S. Pat. No. 4,574,793, and 4-[2-[1-methyl-2-(4-morpholinyl)-ethoxy]ethyl]-morpholine (MEMPE) described in commonly assigned, copending patent application Ser. No. 784,344, filed Oct. 4, 1985, in amounts ranging from about 0.5% to about 5% by weight of the resin system, may be used for this purpose. The MEMPE catalyst disclosed in patent application Ser. No. 784,344, filed Oct. 4, 1985 (now U.S. Pat. No. 4,705,840), which application is incorporated herein by reference, is the presently preferred catalyst system for use in connection with the present invention.

Foaming of the resin which would reduce the porosity of the cured material and its overall strength should be minimized. Foaming occurs because carbon dioxide is released when water reacts with isocyanate groups. The most satisfactory method of minimizing foaming involves the addition of a foam suppressor such as silicone Antifoam A (Dow Corning, Midland, Mich.), DB-100 silicone fluid (Dow Corning), or silicone surfactant L550 or L5303 (available from Union Carbide) to the resin. It is presently preferred to use the Dow Corning DB-100 silicone fluid at a concentration of about 0.1% to about 1% by weight of the resin.

It is also preferred to make the curable resin of the present invention less tacky in accordance with the invention described in commonly assigned, copending U.S. patent application Ser. No. 784,671, filed Oct. 4, 1985 (now U.S. Pat. No. 4,667,661), for "Curable Resin Coated Sheet Having Reduced Tack," filed in the name of Matthew T. Scholz, et al., which application is incorporated herein by reference. Reduced tackiness may be achieved by a number of means as described in application Ser. No. 784,671 (now U.S. Pat. No. 4,667,661), the result being that the kinetic coefficient of friction of the surface of the orthopedic article is less than about 1.2. One technique for achieving such tack reduction is to lightly coat the surfaces of the resin-impregnated nonwoven fabric with a mixture of a polydimethylsiloxane, having a viscosity of at least about 100 centistokes and polyethylene oxide long chain aliphatic hydrocarbon waxes. Alternatively, a small amount of a polyethylene oxid—polypropylene oxide block copolymer (such as Pluronic F-108 available from BASF Wyandotte) may be added to the polyol during prepolymer preparation, after which the polydimethylsiloxane may be sprayed onto the surface of the orthopedic article as before. The polydimethylsiloxene reduces resin tackiness prior to contact with water. The hydrophilic polyethylene oxide materials provide additional tack reduction upon contact with water.

The preparation of the orthopedic casting materials of the present invention generally involves the simple coating of the curable resin onto the nonwoven fabric. The wicking action of the fiber bundles assists in pulling the resin into the interstices, and manual manipulation of the resin into the nonwoven fabric is usually not necessary. It is important, however, that such coating result in sufficient impregnation of the curable resin into the interstices between the fibers of the fiber bundles of the nonwoven fabric. Thus, some manipulation or kneading of the resin into the fabric may sometimes be desirable. Care should be given not to stretch the nonwoven fabric during resin coating so as to preserve the stretchability of the material for its later application around the desired body part.

Orthopedic casting materials prepared in accordance with the present invention are applied in the same fashion as other known orthopedic casting materials. First, the animal body member or part to be immobilized is preferably covered with a conventional cast pad or stockinet to protect the body part. Next, the curable resin is activated, for example, by dipping the orthopedic casting material in water in the case of a water curable resin. Excess water is then squeezed out of the orthopedic casting material, and the material is wrapped or otherwise positioned around the animal body part so as to properly conform thereto. Preferably, the material is then molded and smoothed to form the best fit possible and to properly secure the bone and limb in the desired position. Although often not necessary, if desired, the orthopedic casting material may be held in place during cure by wrapping a stretch bandage or other securing means around the curing orthopedic casting material. When curing is complete, the animal body part is properly immobilized within the orthopedic cast or splint which is formed.

Because of the unique properties of the orthopedic casting materials of the present invention, good tactility and palpability are experienced. Thus, during application of the material to the injured body part, the applier can easily feel through the material to the bone structure therebeneath.

The present invention will be further understood in view of the following examples, which examples are merely illustrative and are not to be considered as comprehensive or limiting in any way.

EXAMPLE 1

In this example, an orthopedic casting material within the scope of the present invention was prepared as follows. First, a spunlaced, hydroentangled scrim of nonwoven polyester, having a basis weight of about 2.1 ounces per square yard (g/m$^2$), was obtained from E.I. duPont de Nemours and Company as Sontara ® polyester fabric, style 8043. (This is the nonwoven fabric shown in FIGS. 1A-1C.) This nonwoven polyester fabric had about 64 openings per square inch, with an average aperture size of about 1.3 mm×2.0 mm. This material was also observed to have an average fiber bundle cross-sectional area of about 0.65 mm$^2$, an average of about 417 fibers per fiber bundle along a given cross-section, an average fiber diameter of about 12 microns, and an average estimated void volume within each fiber bundle of about 93%. Further, the nonwoven polyester fabric had an extensibility of about 22% (when a 2 lb. (908 gram) load was applied across a 1.5 inch (3.8 cm) section of the fabric) in the elongated direction and an extensibility of about 3% (when a 2 lb. (908 gram) load was applied across a 1.5 inch (3.8 cm) section of the fabric) in the transverse direction.

The extensibility of the nonwoven polyester fabric was measured by placing a 4 inch×4 inch (10.2 cm×10.2 cm) piece of the nonwoven polyester fabric in the 1.5 inch (3.8 cm) wide grips of a model 1122 Instron Tensile tester equipped with a 50 lb. (22.7 kg) load cell, which was set for a crosshead speed of 2 inches (5.1 cm) per minute, and a chart speed of 2 inches (5.1 cm) per minute, and a load of 2 pounds (908 grams) was applied to the fabric. The total distance that the nonwoven polyester fabric was stretched, divided by the original length of the fabric (the distance between the grips), was multiplied by 100 to give the percent extensibility or elongation. A load of 2 pounds (908 grams) was chosen in an attempt to approximate the maximum tension which is typically needed when applying an orthopedic casting material to a broken or injured limb.

In this Example 1, several strips of the nonwoven polyester fabric were employed having various dimensions. In this regard, strips were cut having the following dimensions: 1) about 3 inches (7.6 cm) wide and about 144 inches (365.8 cm) long; 2) about 3 inches (7.6 cm) wide and about 41 inches (104.1 cm) long; and 3) about 2 inches (5.1 cm) wide and about 48 inches (121.9 cm) long. These strips were cut such that the length of the strips was coincident with the elongated direction of the fabric material. These strips of fabric were then coated with an isocyanate functional, polyurethane prepolymer resin, such that about 0.20 grams of the resin were applied to each square per inch of the nonwoven fabric (0.031 grams/cm$^2$). Such a resin loading resulted in an orthopedic casting material wherein the resin represented about 82% by weight of the total weight of the material.

The polyurethane prepolymer resin which was utilized in this Example 1 was prepared by the following procedure. A stainless steel reactor was used and was equipped with an axial flow impeller, a nitrogen purge line holding the reactor at a small positive nitrogen pressure, an inlet line for pumping reactants into the reactor, an addition port for adding smaller amounts of chemicals, heating and cooling means, and a stainless steel funnel. The following chemicals listed according to their relative amounts were combined in the reactor as described below.

| Chemical | Wt (%) |
| --- | --- |
| Isonate 143L (Upjohn) | 58.25 |
| Benzoyl chloride | 0.05 |
| Pluronic F-108 (BASF) | 3.95 |
| DB-100 silicone fluid (Dow Corning) | 0.18 |
| 2,6-Di-tert-butyl-4-methyl phenol (BHT) | 0.48 |
| Niax PPG 425 (Union Carbide) | 6.74 |
| Niax PPG 725 (Union Carbide) | 29.03 |
| MEMPE catalyst | 1.32 |

The Isonate 143L was first pumped into the reactor and agitated by starting the impeller. The MEMPE catalyst was then pumped in, an after about 5 minutes of mixing, the Pluronic F-108 was poured into the reactor using the stainless steel funnel. After about 10 minutes of further mixing, the DB-100 silicone fluid was added through the small chemical addition port followed by the addition of the benzoyl chloride in the same manner. After about 5 minutes of further mixing, the Niax PPG 425 polyol was pumped in followed by the BHT which was dissolved in about 15% of the tota) Niax PPG 725 polyol, and then the remaining 85% Niax PPG 725 polyol was added. The mixture was then held at a temperature of about 150° F. (65° C.) with constant agitation for approximately 2 hours and then cooled to room temperature. Within a moisture free chamber, the resultant resin was spread onto the fabric strips, and evenly distributed by manually kneading the resin into the fabric strips.

Following resin impregnation, it was observed that the apertures of the resin impregnated strips were substantially unoccluded. In this regard, the resin adhered to the fiber bundles and kept clear of the apertures such that the average unoccluded area of the apertures after resin impregnation was measured to be about 1.1 mm×1.8 mm, or about 77% of the total area of the apertures. Each resin impregnated strip was then individually sealed in an airtight and water impermeable pouch for later use.

Later, one of the resin impregnated strips (measuring 3 inches (7.6 cm) by 144 inches (365.8 cm)) was removed from its pouch, dipped in water to activate the resin, and excess water was squeezed out. A forearm cast was then constructed by wrapping the resin impregnated strip around a human arm to which a protective stockinet and cast padding had been previously applied. The resin impregnated material demonstrated excellent conformability and extensibility, and allowed for the palpation of the bone structure through the applied material. The material was relatively easy to apply, and water penetration to the core of the material was observed. The cured cast was very smooth and conformed well to the contours of the forearm with little, if any, wrinkling.

When tested, cured ring laminates (having 6 layers) formed from the resin impregnated strips (measuring 3 inches (7.6 cm) by 41 inches (104.1 cm)) of this Example 1 were found to have an average passive water vapor permeability of about 2200 mg $H_2O$ vapor/$m^2$-hr (when measured under an atmosphere of about 45% relative humidity and at a temperature of about 22° C.). Four cured flat laminates (having 6 layers, each measuring 2 inches (5.1 cm) by 2 inches (5.1 cm)) formed from one of the resin impregnated strips (measuring 2 inches (5.1 cm) by 48 inches (121.9 cm)) of this Example 1 were found to have an average air permeability of about 94 $cm^3$ air/second when an air pressure differential of about 6.4 psi (absolute) or 49 g/$cm^2$ was imposed between the two sides of the laminate.

Figure 3A:
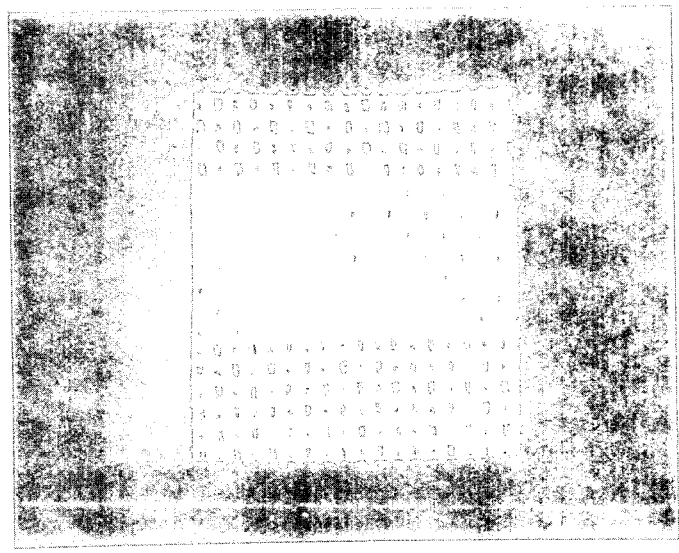
FIG. 3A is a photograph (taken to scale) of two overlapping sheets of the nonwoven polyester fabric of FIG. 1A which have been impregnated with an isocyanate functional polyurethane prepolymer (such that the prepolymer represents about 82% by weight), laminated, and cured with water to form a cured laminate.
Figure 3B:
FIG. 3B is a photograph of a portion of the cured laminate of FIG. 3A shown at a magnification of five times (5×) that of FIG. 3A.
Figure 3B:
Figure 3B:
Figure 3C:
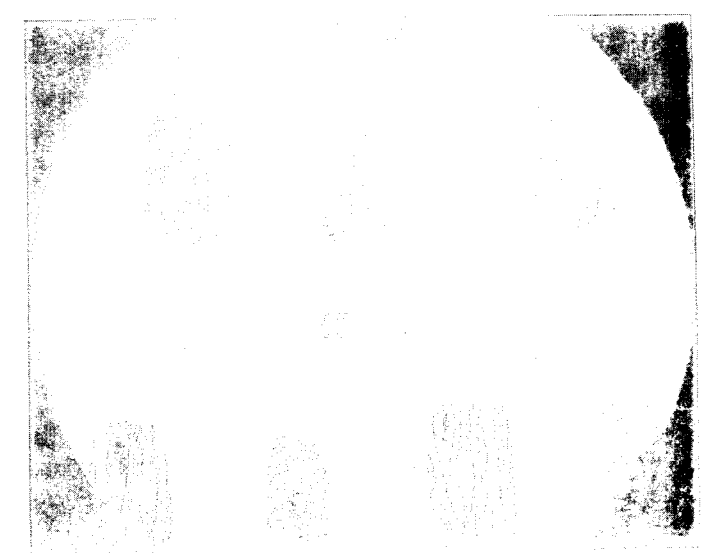
FIG. 3C is a photograph of a portion of the cured laminate of FIG. 3A shown at magnification of ten times (10×) that of FIG. 3A.

A sample of two resin impregnated sheets which were made in accordance with this Example 1, partially overlapped, and cured to form a laminate, is shown in FIGS. 3A-3C.

EXAMPLE 2

In Example 2, five resin impregnated strips (measuring 3 inches (7.6 cm) by 41 inches (184.1 cm)), prepared in accordance with Example 1, were removed from their pouches. These strips were dipped in water at room temperature for about 30 seconds, excess water was squeezed out, and each strip was wound around a 2 inch diameter mandrel covered with a stockinet so as to form a six layer ring therearound. After about 4 minutes, the rings were determined to have set sufficiently, and the rings were removed from the mandrels and allowed to cure for about 72 hours at a temperature of about 72° F. and 55% relative humidity.

Each of the cured rings of Example 2 was placed in a compression test fixture on an Instron Model 1122 apparatus with a 100 lb. (453.6 kg) load cell, so that the overlap seam was not contacted by the penetrating bar of the compression test fixture. The compression test fixture had an upper and a lower base. The lower base was attached to the Instron Tensile Tester, and the upper base was attached to the load cell. The lower base was equipped with two rectangular metal bars dimensioned to approximately ¾" (1.90 cm) wide, ½" (1.27 cm) thick, and 6" (15.2 cm) long, and the bars were attached to the metal base about 1½" (3.81 cm) apart. Each cured ring was in turn placed on these bars and rested against the inside, rounded edges (having a radius of about ⅛" (0.381 cm)). The penetrating bar, approximately ¼" (0.635 cm) wide, ¾" (1.91 cm) thick, and 6" (15.2 cm) long, was mounted to the upper base with a half round edge (having a radius of ⅛" (0.381 cm)) centered above and aligned parallel to the two bars on the lower base. The penetrating bar was lowered against the cured rings, and the maximum load sustained by the rings before failure was recorded.

Following the above procedure, the average ring strength of the rings of this Example 2 was determined to be about 32 lbs/inch (pounds per inch of cylinder length when using a cylinder 3 inches (7.6 cm) long and 2 inches (5.1 cm) in diameter or 5.72 kg/cm. Hence, this example evidences the good ring strengths which can be achieved using the orthopedic casting materials of the present invention.

EXAMPLE 3

In this example, several orthopedic casting materials within the scope of the present invention (having the same three dimensions set forth in Example 1) were prepared in accordance with the procedure and parameters set forth in Example 1 with the following exceptions. In this Example 3, a different nonwoven polyester fabric was employed. The fabric employed in Example 3 was obtained from E.I. duPont de Nemours and Company as Sontara ® polyester fabric, conformable style 8043, set 2, 8 mesh, condition A. (This nonwoven polyester fabric is the subject of FIGS. 2A-2C herein.) Although this fabric also had about 64 apertures per square inch, the apertures were of two different sizes. In this regard, half of the apertures were about 3 mm×1.6 mm, while the other half of the apertures were measured to be about 1.6 mm×1.6 mm. This nonwoven polyester fabric had a basis weight of about 1.60 ounces per square yard (54.4 g/$m^2$). This material was also observed to have an average fiber bundle cross-sectional area of about 0.77 $mm^2$, an average of about 480 fibers per fiber bundle along a given cross-section, an average fiber diameter of about 12 microns, and an average estimated void volume within each fiber bundle of about 92%. Further, the nonwoven polyester fabric had an extensibility of about 17% (when a 2 lb. (908 gram) load was applied across a 1.5 inch (3.8 cm) section of the fabric) in the elongated direction and an extensibility of about 21% (when a 2 lb. (908 gram) load was applied across a 1.5 inch (3.8 cm) section of the fabric) in the transverse direction. All of the other conditions of this Example 3 were identical to Example 1.

However, in this Example 3, after resin application, the average unoccluded area of the apertures of the resin impregnated strips was approximately 87%. Thus, the unoccludability of the apertures resulted in a material with excellent water vapor transition properties. Such air permeability demonstrates the ability of the fiber bundles to pull the resin within the interstices between fibers and thereby leave the apertures substantially unoccluded.

In this regard, when tested, cured ring laminates (having 6 layers, each measuring 2 inches (5.1 cm) by 2 inches (5.1 cm)) formed from the resin impregnated strips (measuring 3 inches (7.6 cm) by 41 inches (104.1 cm)) of this Example 3 were found to have an average passive water vapor permeability of about 2500 mg $H_2O$ vapor/$m^2$-hr (when measured under an atmosphere of about 45% relative humidity and at a temperature of about 22° C.). Four cured flat laminates (having 6 layers, each measuring 2 inches (5.1 cm) by 2 inches (5.1 cm)) formed from one of the resin impregnated strips (measuring 2 inches (5.1 cm) by 48 inches (121.9 cm)) of this Example 3 were found to have an average air permeability of about 250 $cm^3$ air/second when an air pressure differential of about 6.4 psi !absolute) or 449 g/$cm^2$ was imposed between the two sides of the laminate. Furthermore, following the procedure of Example 2, a cured six layer ring formed of the material of this Example 3 was found to have a ring strength of about 35 pounds/inch (6.26 kg/cm).

Figure 4A:
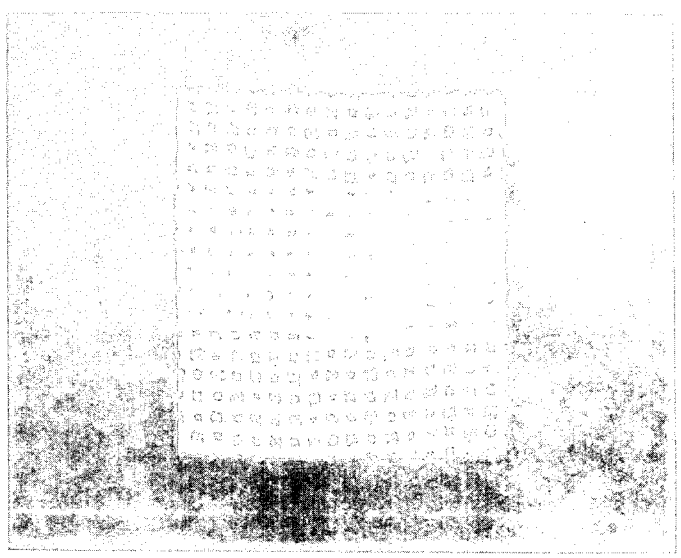
FIG. 4A is a photograph (taken to scale) of two overlapping sheets of the nonwoven polyester fabric of FIG. 2A which have been impregnated with an isocyanate functional polyurethane prepolymer (such that the prepolymer represents about 84% by weight), laminated, and cured with water to form a cured laminate.
Figure 4B:
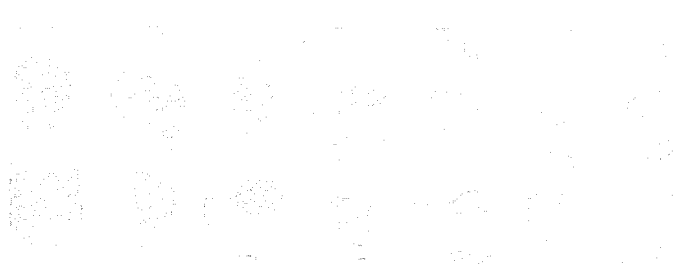
FIG. 4B is a photograph of a portion of the cured laminate of FIG. 4A shown at a magnification of five times (5×) that of FIG. 4A.
Figure 4C:
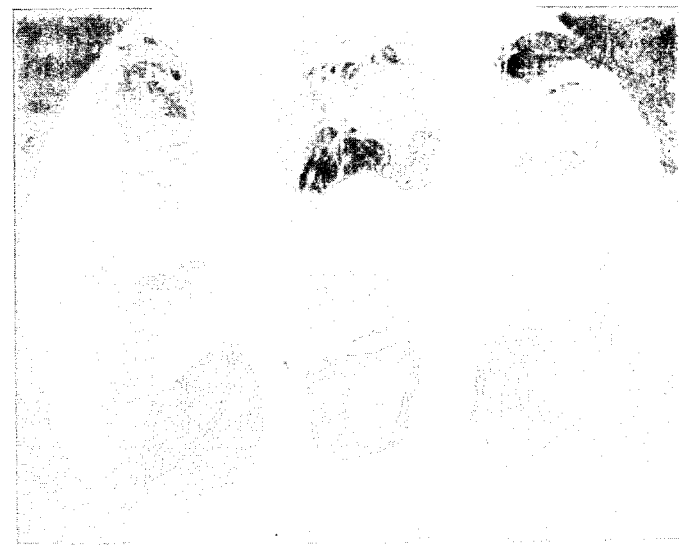
FIG. 4C is a photograph of a portion of the cured laminate of 4A shown at a magnification of ten times (10×) that of FIG. 4A.

A sample of two resin impregnated sheets which were made in accordance with this Example 3, partially overlapped, and cured to form a laminate, is shown in FIGS. 4A–4C.

EXAMPLE 4

In Example 4, a resin impregnated strip (measuring 3 inches (7.6 cm) by 144 inches (365.8 cm)) prepared in accordance with Example 3 was wound around a plastic core having a diameter of about 0.75 inches (1.9 cm), sealed in an airtight pouch, and the pouch was placed in an oven at a temperature of about 150° F. (65° C.) for about one week. After heating, the pouch was opened, and it was observed that relatively little resin had migrated through the rolled material, and virtually none had flowed off of the scrim. This evidences the enhanced ability of the orthopedic rasting materials of the present invention to hold resin and to avoid undesirable migration and flow of the resin out of the material and onto the sides of the pouch during storage.

EXAMPLE 5

In this example, an orthopedic casting material (measuring 3 inches (7.6 cm) by 41 inches (104.1 cm)) within the scope of the present invention was prepared in accordance with the procedure and parameters set forth in Example 3 with the following exceptions. The nonwoven fabric, employed ,in this Example 5 was made of Kevlar ® polyarylamide fiber (instead of polyester fiber), obtained from E.I. duPont de Nemours and Company, Wilmington, Del. under trade designation 039-8K, and had a basis weight of approximately 2.0 oz/sq yd (67.9 g/$m^2$), an extensibility of about 13% in the elongated direction (when a 2 lb. (908 gram) load was applied across a 1.5 inch (3.8 cm) section of the fabric), and an extensibility of about 15% in the transverse direction (when a 2 lb. (908 gram) load was applied across a 1.5 inch (3.8 cm) section of the fabric). The unoccludability of the apertures was similar to that found in Example 3, resulting in a material with excellent water vapor transmission. When tested, a cured laminate of 6 layers of the orthopedic casting material of this Example 5 was found to have a passive water vapor permeability of about 2600 mg $H_2O$ vapor/$m^2$-hr when measured under an atmosphere of about 45% relative humidity and at a temperature of about 22° C. Furthermore, following the procedure of Example 2, a cured six layer ring formed of the material of this Example 5 was found to have a ring strength of about 33 pounds/inch (5.9 kg/cm).

EXAMPLE 6

In this example, an orthopedic casting material within the scope of the present invention may be prepared in accordance with the procedure of Example 1, using a nonwoven cotton fabric having properties as set forth in the above specification, instead of the polyester fabric of Example 1.

EXAMPLE 7

In this example, an orthopedic casting material within the scope of the present invention may be prepared in accordance with the procedure of Example 1, using a nonwoven nylon fabric having properties as set forth in the above specification, instead of the polyester fabric of Example 1.

EXAMPLE 8

In this example, an orthopedic casting material within the scope of the present invention may be prepared in accordance with the procedure of Example 1, using a nonwoven acrylic fabric having properties as set forth in the above specification, instead of the polyester fabric of Example 1.

EXAMPLE 9

In this example, an orthopedic casting material within the scope of the present invention may be prepared in accordance with the procedure of Example 1, using a nonwoven polypropylene fabric having properties as set forth in the above specification, instead of the polyester fabric of Example 1.

EXAMPLE 10

In this example, an orthopedic casting material within the scope of the present invention may be prepared in accordance with the procedure of Example 1, using a nonwoven fiberglass fabric having properties as set forth in the above specification, instead of the polyester fabric of Example 1. The fiberglass nonwoven fabric has a basis weight and is resin loaded within the parameters specifically set forth herein for fiberglass.

From the foregoing, it is seen that the present invention provides new orthopedic casting materials which do not employ plaster of Paris and yet exhibit good tactile manipulation and moldability during application so that the underlying bone structure of the limb can be properly palpated through the material during application. Further, the present invention provides orthopedic casting materials which preserve the advantages of non-plaster of Paris casting materials and which can be made to be less expensive than other non-plaster of Paris casting materials presently available.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An orthopedic support material, comprising:
   a nonwoven, stretchable fabric comprising a pattern of fiber bundles and apertures between said fiber bundles, each said fiber bundle comprising a plurality of fibers having interstices therebetween, the average size of said apertures being from about 0.3 mm$^2$ to about 16 mm$^2$; and
   a curable prepolymer resin which is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material.

2. An orthopedic support material as defined in claim 1 wherein, prior to impregnation with said prepolymer resin, said nonwoven fabric has from about 10% to about 45% extensibility in the elongated direction when a 2 pound load is applied across a 1.5 inch section of the nonwoven fabric.

3. An orthopedic support material as defined in claim 1 wherein the fibers in each said fiber bundle are oriented so as to be generally parallel to one another.

4. An orthopedic support material, comprising:
   a nonwoven, stretchable fabric comprising a pattern of fiber bundles and apertures between said fiber bundles, each said fiber bundle comprising a plurality of fibers having interstices therebetween the average cross-sectional area of each said fiber bundle being from about 0.2 mm$^2$ to about 1.2 mm$^2$; and
   a curable prepolymer resin which is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material.

5. An orthopedic support material as defined in claim 1 wherein a cross-section of each said fiber bundle contains an average of at least about 100 of said fibers.

6. An orthopedic support material as defined in claim 1 wherein the average diameter of each individual fiber in each said fiber bundle is from about 1 micron to about 30 microns.

7. An orthopedic support material as defined in claim 1 wherein the average void volume within each said fiber bundle is from about 20% to about 98% of the total volume occupied by the fiber bundle.

8. An orthopedic support material, comprising:
   a nonwoven, stretchable fabric comprising a pattern of fiber bundles and apertures between said fiber bundles, each said fiber bundle comprising a plurality of fibers having interstices therebetween, the average size of said apertures being from about 0.3 mm$^2$ to about 16 mm$^2$, the average cross-sectional area of each said fiber bundle being from about 0.2 mm$^2$ to about 1.2 mm$^2$, the weight of said nonwoven fabric being from about 1 ounce per square yard to about 2.5 ounces per square yard; and
   a curable prepolymer resin which is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material.

9. An orthopedic support material as defined in claim 1 wherein said nonwoven fabric has from about 15 to about 400 of said apertures per square inch.

10. An orthopedic support material, comprising:
    a nonwoven, stretchable fiberglass fabric comprising a pattern of fiber bundles and apertures between said fiber bundles, each said fiber bundle comprising a plurality of fibers having interstices therebetween, the average size of said apertures being from about 0.3 mm$^2$ to about 16 mm$^2$, the weight of said nonwoven fiberglass fabric being from about 1.8 ounces per square yard to about 4.6 ounces per square yard; and
    a curable prepolymer resin which is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material.

11. An orthopedic support material as defined in claim 1 wherein said nonwoven fabric is a spunlaced, hydroentangled, nonwoven fabric.

12. An orthopedic support material as defined in claim 1 wherein said nonwoven fabric comprises polyester.

13. An orthopedic support material as defined in claim 1 wherein said nonwoven fabric comprises cotton.

14. An orthopedic support material as defined in claim 1 wherein said nonwoven fabric comprises nylon.

15. An orthopedic support material as defined in claim 1 wherein said nonwoven fabric comprises acrylic fibers.

16. An orthopedic support material as defined in claim 1 wherein said nonwoven fabric comprises polypropylene.

17. An orthopedic support material as defined in claim 1 wherein said nonwoven fabric comprises fiberglass.

18. An orthopedic support material as defined in claim 1 wherein said nonwoven fabric comprises polyarylamide.

19. An orthopedic support material as defined in claim 1 wherein said nonwoven fabric comprises carbon.

20. An orthopedic support material as defined in claim 1 wherein said prepolymer resin is an isocyanate functional, polyurethane prepolymer resin.

21. An orthopedic support material as defined in claim 1 wherein sufficient prepolymer resin is impregnated into the nonwoven fabric such that the resin represents from about 65% to about 90% by weight of the total weight of the orthopedic support material.

22. An orthopedic support material as defined in claim 1 wherein from about 0.1 grams to about 0.3 grams of prepolymer resin are applied to each square inch of the nonwoven fabric.

23. An orthopedic support material as defined in claim 1 wherein from about 60% to about 100% of the total area of said apertures remains unoccluded after impregnation of said prepolymer resin into said nonwoven fabric.

24. An orthopedic support material, comprising:
a nonwoven, stretchable fabric comprising a pattern of fiber bundles and apertures between said fiber bundles, each said fiber bundle comprising a plurality of fibers having interstices therebetween; and
a curable prepolymer resin which is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material;
wherein upon curing a laminate comprising 6 layers of said material said laminate has a passive water vapor permeability of at least about 2000 mg $H^2O$ vapor/$m^2$-hr when measured under an atmosphere of about 45% relative humidity and at a temperature of about 22° C.

25. An orthopedic support material, comprising:
a nonwoven, stretchable fabric comprising a pattern of fiber bundles and apertures between said fiber bundles, each said fiber bundle comprising a plurality of fibers having interstices therebetween; and
a curable prepolymer resin which is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material;
wherein upon curing a laminate comprising 6 layers of said material, with each layer having an area of about 4 $in^2$, said laminate has an air permeability of from about 30 $cm^3$ air/second to about 370 $cm^3$ air/second when an air pressure differential of about 6.4 psi exist between two sides of the laminate.

26. An orthopedic support material as defined in claim 1 wherein after curing a ring laminate comprising 6 layers of said material said laminate has a ring strength of at least about 10 pounds per inch of ring length were the ring laminate has a length of 3 inches and a diameter of 2 inches.

27. An orthopedic casting material, comprising:
a nonwoven sheet of polyester comprising a pattern of fiber bundles and apertures between said fiber bundles, each said fiber bundle comprising a plurality of fibers having interstices therebetween, the average size of said apertures being from about 0.3 $mm^2$ to about 16 $mm^2$, said nonwoven polyester sheet having from about 10% to about 45% extensibility along its length when a 2 pound force is applied across a 1.5 inch section of said sheet; and
an isocyanate functional, polyurethane prepolymer resin which is impregnated into the interstices between said fibers of said fiber bundles in sufficient quantity such that the resin represents from about 65% to about 90% by weight of the total weight of the orthopedic casting material and impart sufficient strength to the material upon curing to be used as an orthopedic casting material, said apertures remaining substantially unoccluded such that upon curing a laminate comprising 6 layers of said material said laminate has a water vapor permeability of at least about 2000 mg $H_2O$ vapor/$m^2$-hr when measured under atmosphere of about 45% relative humidity and at a temperature of about 22° C., thereby substantially avoiding skin maceration.

28. An orthopedic casting material as defined in claim 27:
wherein the fibers in each said fiber bundle are oriented so as to be generally parallel to one another and wherein a cross-section of each said fiber bundle contains an average of at least about 100 of said fibers;
wherein said nonwoven polyester sheet has a weight of from about 1 ounce per square yard to about 2.5 ounces per square yard; and
wherein said nonwoven polyester sheet has from about 15 to about 400 of said apertures per square inch.

29. A method of forming an orthopedic cast on an animal body member, comprising the steps of:
covering said body member with a protective fabric which is water vapor permeable;
wetting with water an orthopedic casting material comprising:
a nonwoven sheet comprising a pattern of fiber bundles and apertures between said fiber bundles, each said fiber bundle comprising a plurality of fibers having interstices therebetween, the average size of said apertures being from about 0.3 $mm^2$ to about 16 $mm^2$; and
a water curable prepolymer resin which is impregnated into the interstices between said fibers of said fiber bundles so as to impart sufficient strength to the material upon curing to be used as an orthopedic casting material while leaving the apertures between fiber bundles substantially unoccluded so as to permit sufficient water vapor permeability thought the cured material to substantially avoid skin maceration; and
wrapping said body member with said wetted orthopedic casting material and allowing said material to harden to form said orthopedic cast.

30. An orthopedic support material as defined in claim 1 wherein said nonwoven fabric is a spunlaced, hydroentangled fabric and has about 64 apertures per square inch.

31. An orthopedic support material as defined in claim 30 wherein said nonwoven fabric has an average aperture size of about 2.6 $mm^2$.

32. An orthopedic support material as defined in claim 30 wherein said nonwoven fabric has average aperture size of about 4.8 $mm^2$ for about 50% of the apertures and an average aperture size of about 2.5-2.6 $mm^2$ for the other 50% of the apertures.

33. An orthopedic support material as defined in claim 1 wherein said nonwoven fabric is a spunlaced, hydroentangled, nonwoven polyester fabric and wherein said nonwoven fabric has:
about 22% extensibility in the elongated direction when a 2 pound load is applied across a 1.5 inch section of the nonwoven fabric;
an average fiber bundle cross-sectional area of about 0.65 $mm^2$;

an average of about 417 fibers per fiber bundle cross-section;

an average fiber diameter of about 12 microns;

an average fiber bundle void volume of about 93%;

a weight of about 2.1 ounces per square yard;

about 64 apertures per square inch; and an average aperture size of about 1.3 mm×2 mm.

34. An orthopedic support material as defined in claim 1 wherein said nonwoven fabric is a spunlaced, hydroentangled, nonwoven polyester fabric and wherein said nonwoven fabric has:

about 17% extensibility in the elongated direction when a 2 pound load is applied across a 1.5 inch section of the nonwoven fabric;

an average fiber bundle cross-sectional area of about 0.77 mm$^2$;

an average of about 480 fibers per fiber bundle cross-section;

an average fiber diameter of about 12 microns;

an average fiber bundle volume of about 92%;

a weight of about 1.6 ounces per square yard;

about 64 apertures per square inch; and an average aperture size of about 3 mm×1.6 mm for about 50% of the apertures and an average aperture size of about 1.6 mm×1.6 mm for the other 50% of the apertures.

35. An orthopedic support material as defined in claim 1 wherein the average size of said apertures is from about 1.2 mm$^2$ to about 9 mm$^2$.

36. An orthopedic support material as defined in claim 1 wherein the average cross-sectional area of each said fiber bundle is from about 0.2 mm$^2$ to about 1.2 mm$^2$.

37. An orthopedic support material as defined in claim 1 wherein the weight of said nonwoven fabric is from about 1 ounce per square yard to about 2.5 ounces per square yard.

38. An orthopedic support material as defined in claim 1 wherein upon curing a laminate comprising 6 layers of said material said laminate has a passive water vapor permeability of at least about 2000 mg H2O vapor/m$^2$-hr when measured under an atmosphere of about 45% relative humidity and at a temperature of about 22° C.

39. An orthopedic support material as defined in claim 1 wherein upon curing a laminate comprising 6 layers of said material, with each layer having an area of about 4 in$^2$, said laminate has an air permeability of from about 30 cm$^3$ air/second to about 370 cm$^3$ air/second when an air pressure differential of about 6.4 psi exists between two sides of the laminate.

40. An orthopedic support material as defined in claim 28 wherein the average size of said apertures is from about 1.2 mm$^2$ to about 9 mm$^2$.

41. An orthopedic support material as defined in claim 28 wherein the average cross-sectional area of each said fiber bundle is from about 0.2 mm$^2$ to about 1.2 mm$^2$.

42. An orthopedic support material as defined in claim 28 wherein upon curing a laminate comprising 6 layers of said material, with each layer having an area of about 4 in$^2$, said laminate has an air permeability of from about 30 cm$^3$ air/second to about 370 cm$^3$ air/second when an air pressure differential of about 6.4 psi exists between two sides of the laminate.

43. A method as defined in claim 29 wherein the average size of said apertures is from about 1.2 mm$^2$ to about 9 mm$^2$.

44. A method as defined in claim 29 wherein the average cross-sectional area of each said fiber bundle is from about 0.2 mm$^2$ to about 1.2 mm$^2$.

45. A method as defined in claim 29 wherein said nonwoven sheet comprises polyester.

46. A method as defined in claim 29 wherein the weight of said nonwoven sheet is from about 1 ounce per square yard to about 2.5 ounces per square yard.

47. A method as defined in claim 29 wherein upon curing a laminate comprising 6 layers of said orthopedic casting material said laminate has a passive water vapor permeability of at least about 2000 mg H$_2$O vapor/m$^2$-hr when measured under an atmosphere of about 45% relative humidity and at a temperature of about 22° C.

48. A method as defined in claim 29 wherein upon curing a laminate comprising 6 layers of said orthopedic casting material, with each layer having an area of about 4 in$^2$, said laminate has an air permeability of from about 30 cm$^3$ air/second to about 370 cm$^3$ air/second when an air pressure differential of about 6.4 psi exists between two sides of the laminate.

49. An orthopedic support material as defined in claim 4 wherein the average cross-sectional area of each said fiber bundle is from about 0.4 mm$^2$ to about 1 mm$^2$.

50. An orthopedic support material as defined in claim 1 wherein the weight of said nonwoven fabric is from about 1.2 ounces per square yard to about 2.1 ounces per square yard.

51. An orthopedic support material as defined in claim 10 wherein the average size of said apertures is from about 0.3 mm$^2$ to about 16 mm$^2$.

* * * * *

UNITED STATES PATENT AND TRADEMARK OFFICE
CERTIFICATE OF CORRECTION

PATENT NO. : 4,841,958

DATED : June 27, 1989

INVENTOR(S) : Dean A. Ersfeld and Paul E. Hansen

It is certified that error appears in the above-identified patent and that said Letters Patent is hereby corrected as shown below:

Col. 3, line 2, "wit" should read --with--.

Col. 3, line 15, "IA" should read --1A--.

Col. 5, line 65, "he" should read --the--.

Col. 5, line 68, "weigh" should read --weight--.

Col. 6, line 2, "orthopedic material" should read --orthopedic casting material--.

Col. 6, line 4, "within scope" should read --within the scope--.

Col. 6, line 5, "0.3 grams" should read --about 0.3 grams--.

Col. 6, line 7, "resin being" should read --resin loading being--.

Col. 6, line 33, "total volume," should read --total volume--.

Col. 8, line 21, "invention at" should read --invention, at--.

Col. 10, line 34, "Sontata" should be --Sontara--.

Col. 12, line 25, after "pliable" insert --and conformable and should adhere to itself. Then in a--.

Col. 13, line 28, "2,4,-diphenylmethane" should read --2,4'-diphenylmethane--.

Col. 14, line 29, after "1985" insert --(now U.S. Patent No. 4,705,840)--.

UNITED STATES PATENT AND TRADEMARK OFFICE
CERTIFICATE OF CORRECTION

PATENT NO. : 4,841,958  
DATED : June 27, 1989  
INVENTOR(S) : Dean A. Ersfeld and Paul E. Hansen Page 2 of 3

It is certified that error appears in the above-identified patent and that said Letters Patent is hereby corrected as shown below:

Col. 14, line 67, "oxid" should read --oxide--.

Col. 15, line 4, "polydimethylsiloxene" should read --polydimethylsiloxane--.

Col. 15, line 60, "$(g/m^2)$" should read --$(71.3\ g/m^2)$--.

Col. 16, line 67, "an" should read --and--.

Col. 17, line 7, "tota)" should read --total--.

Col. 17, line 54, "49" should read --449--.

Col. 19, line 24, "!absolute)" should read --(absolute)--.

Col. 19, line 46, "rasting" should read --casting--.

Col. 19, line 57, remove both commas

Col. 21, line 37, insert a comma after "therebetween"

Col. 21, line 63, "fib®r" should read --fiber--.

Col. 23, line 23, "$H^2O$" should read --$H_2O$--.

Col. 23, line 45, "exist" should read --exists--.

Col. 23, line 50, "were" should read --where--.

Col. 23, line 68, "impart" should read --imparts--.

Col. 24, line 7, after "under" insert --an--.

Col. 24, line 43, "thought" should read --through--.

UNITED STATES PATENT AND TRADEMARK OFFICE
CERTIFICATE OF CORRECTION

PATENT NO. : 4,841,958

DATED : June 27, 1989

INVENTOR(S) : Dean A. Ersfeld and Paul E. Hansen

It is certified that error appears in the above-identified patent and that said Letters Patent is hereby corrected as shown below:

Col. 24, line 56, after "has" insert --an--.

Col. 25, line 21, after "bundle" insert --void--.

Col. 25, line 43, "H2O" should read --$H_2O$--.

Signed and Sealed this

Tenth Day of April, 1990

Attest:

HARRY F. MANBECK, JR.

*Attesting Officer*    *Commissioner of Patents and Trademarks*